United States Patent [19]

Bass et al.

[11] Patent Number: 4,990,367
[45] Date of Patent: Feb. 5, 1991

[54] CANINE DISTEMPER VIRUS VACCINE

[75] Inventors: Edmund P. Bass, Menlo Park; William H. Kelsey, Alameda, both of Calif.; Michael D. McFarland, Boone, Iowa

[73] Assignee: Diamond Scientific Company, Des Moines, Iowa

[21] Appl. No.: 463,763

[22] Filed: Jan. 12, 1990

Related U.S. Application Data

[60] Continuation of Ser. No. 351,774, May 15, 1989, abandoned, which is a continuation of Ser. No. 115,345, Nov. 2, 1987, abandoned, which is a division of Ser. No. 23,814, Mar. 9, 1987, abandoned.

[51] Int. Cl.$^5$ .................................... A61K 39/12
[52] U.S. Cl. ................................................ 424/89
[58] Field of Search ...................................... 424/89

[56] References Cited

U.S. PATENT DOCUMENTS

| | | | |
|---|---|---|---|
| 1,967,476 | 7/1934 | Little | 424/89 |
| 2,136,131 | 11/1938 | Green | 424/89 |
| 2,271,818 | 2/1942 | Green | 424/89 |
| 2,271,819 | 2/1942 | Green | 424/89 |
| 2,720,484 | 10/1955 | Meadows et al. | 424/89 |
| 2,965,544 | 12/1960 | Cabasso | 424/89 |
| 3,080,291 | 3/1963 | Sinha et al. | 424/89 |
| 3,098,011 | 7/1963 | Rockborn | 424/89 |
| 3,318,775 | 5/1967 | Melvin et al. | 424/89 |
| 3,354,038 | 11/1967 | Bass | 424/89 |
| 3,420,934 | 1/1969 | Ackermann | 424/89 |
| 3,462,526 | 8/1969 | de Ratuld et al. | 424/89 |
| 3,470,294 | 9/1969 | Drager et al. | 424/89 |
| 3,594,471 | 7/1971 | Hertzberger et al. | 424/89 |
| 3,636,196 | 1/1972 | Bauer et al. | 424/89 |
| 3,836,626 | 9/1974 | Lavender | 424/89 |
| 3,886,270 | 5/1975 | Ackermann | 424/89 |
| 4,004,974 | 1/1977 | Chumakov et al. | 424/89 |
| 4,036,952 | 7/1977 | Bauer et al. | 424/89 |
| 4,071,618 | 1/1978 | Konobe et al. | 424/89 |
| 4,112,068 | 9/1978 | Cabasso | 424/89 |
| 4,347,239 | 8/1982 | Bass et al. | 424/89 |
| 4,358,438 | 11/1982 | Bijlenga | 424/89 |
| 4,545,987 | 10/1985 | Giles et al. | 424/89 |
| 4,556,556 | 12/1985 | Wiesehahn et al. | 424/89 |
| 4,567,042 | 1/1986 | Acree et al. | 424/89 |
| 4,567,043 | 1/1986 | Acree et al. | 424/89 |
| 4,693,981 | 9/1987 | Wiesehahn et al. | 424/89 |

OTHER PUBLICATIONS

Appel et al, Archives of Virology 82:73–82 (1984) Measles Virus and Inactivated Canine Distemper Virus Induce Incomplete Immunity to Canine Distemper.

Appel, M., 1984, Measles virus and inactivated canine distemper virus induc incomplete immunity to canine distemper, Arch. Virol. 82: 73–82.

Gillespie, J., 1965, A study of inactivated distemper virus in the dog, Cornell Vet. 55: 3–8.

Sheshberadaron, H., 1986, The antigenic relationship between measles, canine J. Gen. Virol. 67: 1381–1392.

Norrby, E., 1986, Protection against canine distemper virus in dogs after immunization with isolated fusion protein, J. Virol. 58: 536–541.

McCormick, A., 1983, Canine distemper in African cape hunting dogs (Lycoan pictus)—possibly vaccine induced, J. Zoo. Anim. Med. 14: 66–71.

Halbrooks, R., 1982, Response of gray foxes to modified live virus canine distemper vaccines, J. Am. Vet. Med. Assoc. 179: 1170–1174.

Hartley, W., 1974, A post-vaccinal inclusion body encephalitis in dogs, Vet. Pathol. 11: 301–312.

McAnulty, J., 1985, Thrombocytopenia associated with vaccination of a dog with a modified live paramyxovirus vaccine. J. Am. Vet. Med. Assoc. 186: 1217–1219.

McLaughlin, B., 1985, Canine distemper viral inclusions in blood cells of four vaccinated dogs. Canadian Vet. J. 26:368–372.

Krakowka, S., 1982, Canine parvovirus infection potentiates canine distemper J. Am. Vet. Med. Assoc. 180: 137–139.

Wilson, N., 1981, Distemper vaccine breakdowns. Vet. Rec. 108: 171.

Appel, M., 1978, Reversion to virulence of attenuated canine distemper virus in vivo and in vitro. J. Gen. Virol. 41: 385–393.

*Primary Examiner*—Ronald W. Griffin
*Attorney, Agent, or Firm*—Joseph C. Gil; Lyndanne M. Whalen

[57] ABSTRACT

A vaccine composition for animals susceptible to infection by canine distemper virus. The vaccine comprises a small but immunologically effective amount of an inactivated canine distemper virus in combination with a non-toxic pharmaceutically acceptable immunologic adjuvant. A preferred method of inactivation of canine distemper virus by either exposure of the virus to an inactivating effective amount of binary ethyleneimine or alternatively exposure of the virus to long wavelength ultraviolet light in the presence of a furocoumarin.

8 Claims, No Drawings

CANINE DISTEMPER VIRUS VACCINE

This application is a continuation of application Ser. No. 07/351,774 filed May 15, 1989, now abandoned, which is a continuation of application Ser. No. 07/115,346, filed Nov. 2, 1987, now abandoned, which is a Divisional of Application Ser. No. 07/023,814 filed Mar. 9, 1987, now abandoned.

BACKGROUND OF THE INVENTION

Canine distemper is one of the most serious viral diseases of dogs. The disease is highly contagious and is characterized by severe morbidity and high mortality. Modified live canine distemper virus vaccines are currently available in the United States. They do provide protective immunity to distemper, but such vaccines may revert to virulence, may cause immunosupression following vaccination, and have been shown to cause mortality in non-canie speices. There is therefore a real need for an efficacious, inactivated canine distemper virus vaccine, which eliminates the serious problems associated with modified live canine distemper virus vaccines.

It is therefore a primary objective of the present invention to develop an inactivated canine distemper virus vaccine which substantially eliminates the serious problems, and risks, associated with modified live canine distemper virus vaccines.

It is another primary objective of the present invention to develop a canine virus vaccine containing inactivated canine distemper virus, which although inactivated still substantially retains its immunogenicity.

Another objective of the present invention is to develop a method for inactivating canine distemper virus.

Yet another objective of the present invention is to develop a preferred method of inactivating canine distemper virus which nevertheless allows the virus to retain its immunogenicity, with the method involving either exposure of the virus to an inactivating effective amount of binary ethyleneimine or alternatively to exposure of the virus to an inactivating effective amount of furocoumarin in the presence of long wavelength ultraviolet light.

It is a still further objective of the present invention to develop a method and composition for effective vaccination against canine distemper virus which contains an inactivated canine distemper virus, preferably which employs one of the above described procedures.

The method and manner of accomplishing each of the above objectives will become apparent from the detailed description of the invention which will follow hereinafter.

SUMMARY OF THE INVENTION

The present invention is directed to a new vaccine composition for canine distemper virus. It is also directed to a method for inactivating canine distemper virus, such that the virus while inactivated, nevertheless substantially retains its immunogenicity. The method preferably involves one of two successful inactivation procedures. The first involves inactivating the virus with binary ethyleneimine. The second method involves inactivating the virus by irradiation with long wavelength ultraviolet light in the presence of a furocoumarin.

The composition of this invention comprises a small but immunologically effective amount of the inactivated canine distemper virus in combination with a non-toxic pharmaceutically acceptable immunologic adjuvant. The invention in another aspect relates to a method for protecting mammals susceptible to infection by canine distemper virus, preferably dogs, from infection by said virus.

DETAILED DESCRIPTION OF THE INVENTION

In this invention, inactivated vaccines are manufactured for the protection of mammalian species, in particular the canine, from severe clinical signs and mortality resulting from infection with canine distemper virus (CDV). The vaccines are inactivated, preferably either by the addition of binary ethyleneimine to virus fluids, or by combining virus fluids with a sufficient amount of a furocoumarin to provide for complete inactivation of CDV upon irradiation with long wavelength ultraviolet light (UVA), preferably while maintaining an inert atmostphere. The resulting inactivated virus preparation may be stored until used for vaccination.

Any strain of CDV may be inactivated for use in this invention. Of particular interest is the Rockborn strain, but other strains such as Snyder-Hill, Onderstepoort, etc. may be used.

In preparing the vaccine, virulent CDV is grown in cultured mammalian cells in conventional virus growth conditions. Examples of cells used are the DKF (dog kidney) cell line, and tertiary canine kidney cells. The host cells may be seeded with virus at the time of cell planting, or with a CDV-containing media change when the cell monolayer is 90-100% confluent. The multiplicity of infection (MOI) ratio may be from about 0.001 to about 0.05, preferably about 0.01. Any appropriate mammalian cell growth medium, such as Eagle's Minimum Essential Medium, containing bovine serum at from 0-10%, and antibiotics, is used to produce the viral fluids.

Infected cell cultures are maintained in a temperature range of from about 35° C. to about 40° C. for from 2 to about 7 days post seeding at which time virus-containing fluids are harvested. The CDV infected cultures may be refed with cell growth medium, which may be harvested after an additional 2 to 5 days incubation. Virus fluids are harvested into sterile containers and may be clarified by filtration. The virus fluids may further be concentrated, either prior to or post inactivation, using conventional ultrafiltration technology (e.g., Millipore Pellicon system XX42ASY60 with a cassette having a normal exclusion limit of $10^5$ daltons such as Millipore PTHK000C5).

The virulent canine distemper virus after harvest is ready for inactivation. The inactivation must be by a technique which destroys the virus' ability to replicate, but at the same time does not destroy the immunological activity of the inactivated virus. Heretofore there never has been a successful inactivated canine distemper virus vaccine. In this invention there is provided a virus which is both inactivated and at the same time retains immunogenicity.

As used herein, the term "inactivated" refers to previously virulent virus which have undergone treatment to inactivate, kill, or otherwise modify them to substantially eliminate their virulent properties while yet retaining their characteristic property of immunogenicity.

In accordance with this invention, there are two preferred techniques for inactivating and retaining immunogenicity. In the first of these techniques, CDV fluids may be inactivated with binary ethyleneimine (BEI). BEI is prepared by adding 1.0 N sodium hydroxide to a 5% solution of bromoethylamine hydrobromide followed by incubation at, for example, about 37° C. for 60 minutes. The resulting BEI inactivant is added to virus fluids to a final concentration of from about 0.005 to about 0.01 molar. The inactivating virus fluids are incubated at from about 4° C. to about 38° C. for an interval of from about 24 to about 72 hours. The BEI is subsequently neutralized, for example, by the addition of a 50% solution of sodium thiosulfate in sufficient quantity to equal ten times the molarity of the BEI. It should be understood that the above specific technique for inactivation for binary ethyleneimine is exemplary only. That is, there may be some modifications in concentrations, temperature ranges, etc. such that the inactivation is still effectively accomplished. Generally speaking, the temperature range during the binary ethyleneimine inactivation should be from about $-10°$ C. to about 40° C.

Alternatively, virus fluids may be inactivated by furocoumarin compounds. These compounds are primarily illustrated by the class of compounds referred to as psoralens, which includes psoralen and pharmaceutically acceptable derivatives thereof, where the substituents can be: alkyl, preferably of from 1 to 3 carbon atoms, e.g., methyl, ethyl and propyl; alkoxy, particularly of from 1 to 3 carbon atoms, e.g., methoxy; and substituted alkyl, of $C_1$ to $C_6$, preferably of $C_1$ to $C_3$ having from 1 to 2 heteroatoms, which can be oxy, particularly hydroxy or alkoxy of from 1 to 3 carbon atoms, e.g., hydroxymethyl and methoxymethyl; or amino, including mono- and dialkyl amino or aminoalkyl, having a total of from $C_1$ to $C_6$ carbon atoms, e.g., amino-methyl. There may be from 1 to 5, usually 2 to 4 substituents, which will normally be at the 4, 5, 8, 4' and 5' positions, particularly at the 4' position. Illustrative compounds include: 5-methoxypsoralen; 8-methoxypsoralen (8-MOP); 4, 5', 8-trimethylpsoralen (TMP); 4'-hydroxymethyl- 4,5',8-trimethylpsoralen (HMT); 4'-aminomethyl-4, 5',8-trimethyl-psoralen (AMT);4-methylpsoralen; 4,4'-dimethylpsoralen; 4,5'-dimethylpsoralen; 4',8- dimethylpsoralen; and 4'-methoxy-methyl-4,5',8- trimethylpsoralen. For further details on suitable psoralens see Giles et. al., U.S. Pat. No. 4,545,987 issued Oct. 8, 1985, and Wiesehahn et al., U.S. Pat. No. 4,556,556 issued Dec. 3, 1985, the disclosures of which are incorporated herein by reference.

The furocoumarins may be used individually or in combination. Each of the furocoumarins may be present in amounts ranging from about 0.01 $\mu$g/ml (micrograms/ml) to about 1 mg/ml, preferably a lower level of from about 0.5 $\mu$g/ml, and most preferably there not being less than about 1 $\mu$g/ml nor more than about 1 mg/ml of furocoumarins.

In carrying out the process of this invention the furocoumarin(s), in an appropriate solvent which is substantially inert and sufficiently polar to allow for disolution of the furocoumarin(s) are combined with the viral suspension, conveniently a viral suspension in an aqueous buffered medium, such as used for storage. The amount of virus will generally be about $1 \times 10^4$ to $10^8$, more usually about $1 \times 10^5$ to $10^7$ and preferably about $1 \times 10^{5.8}$ to $1 \times 10^{6.2}$ CCID$_{50}$ml (Cell Culture Infectious Dose). The amount of solvent which is used to dissolve the furocoumarin should be sufficiently small so as to readily dissipate in the aqueous viral suspension and have little, if any, effect on the results.

The psoralen(s) may be added to the viral suspension in a single addition or in multiple additions, where the virus is irradiated between additions. Usually, the number of additions can be from about 1 to about 5, more usually from about 1 to about 4, and preferably from about 2 to about 4. The total amount of psoralen(s) which can be added should be sufficient to provide a concentration of at least about 0.01 mg/ml to about 1 mg/ml, usually not more than about 0.75 mg/ml and preferably not more than about 0.5 mg/ml. Since a proportion of the psoralen(s) will have reacted with the canine distemper virus RNA between additions, the total concentration in solution will generally not exceed about 0.3 mg/ml.

The total time for the irradiation will vary depending upon the light intensity, the concentration of the psoralen(s), the concentration of the virus, and the manner of irradiation of the virus, where the intensity of the irradiation may vary. The total time will usually be at least from about 10 minutes to not more than about 60 hours, generally ranging from about 2 hours to 50 hours. The times between additions of for example psoralen, where the psoralen is added incrementally, will generally vary from about 1 hour to 24 hours, more usually from about 2 hours to 20 hours.

The temperature for the irradiation is preferably under 25° C., more preferably under 20° C., and will generally range from about $-10°$ to about 15° C., more usually from about 0° to about 10° C.

The irradiation is normally carried out in an inert atmosphere, where all or substantially all of the air has been removed. Inert atmostpheres include nitrogen, helium, argon, etc.

The light which is employed will generally have a wavelength in the range from about 300 nm to 400 nm. The intensity will generally range from about 0.1 mW/cm$^2$ to about 10 W/cm$^2$.

Optionally, a small amount of a single oxygen scavenger may be included during the virus inactivation. Singlet oxygen scavengers include ascorbic acid, dithioerythritol, sodium thionite, glutathione, superoxide dismutase etc. The amount of scavenger will generally be at a concentration of about 0.001 M to 0.5 M, more usually at about 0.05 M to 0.2 M, where the addition may be made in a single or multiple additions.

During irradiation, the medium may be maintained still, stirred or circulated and may be either continuously irradiated or be subject to alternating periods of irradiation and non-irradiation. The circulation may be in a closed loop system or in a single pass system ensuring that all of the sample has been exposed to irradiation.

It may be at times desirable to remove the unexpended furocoumarin and/or its photo-breakdown products from the irradiation mixture. This can be readily accomplished by one of several standard laboratory procedures such as dialysis across an appropriately sized membrane or through an appropriately sized hollow fiber system after completion of the irradiation. Alternatively, one may use affinity columns for one or more of the low molecular weight materials to be removed.

Either of the above preferred inactivating procedures (i.e. BEI or furocoumarin technique) may be employed with satisfactory results. However, it is preferred that one employ the technique of use of furocoumarins coupled with irradiation, since psoralen inactivated CDV induces higher serum neutralization antibody titers in vaccinated dogs, compared to BEI inactivated CDV vaccine.

It may also be possible to use other inactivating techniques, and this invention contemplates such. Thus, use of for example cis-platinum inactivation may be possible. In summary, any technique that will allow inactivation while still retaining immunogenicity may be employed. This includes, but is not limited to, the preferred techniques of use of BEI or furocoumarin, and others as well as acetyl ethyleneimine, beta-propriolactone, formalin, phenol, and ultraviolet radiation or gamma radiation.

In preparation of the vaccine, the inactivated collected canine distemper virus is mixed with a non-toxic pharmaceutically acceptable immunologic adjuvant such as Freund's complete adjuvant, aluminum hydroxide or oil-in-water or water-in-oil adjuvants. Also, Interlukin-1, or other immuno-enhancing substances may be used. Preparation of the vaccine entails mixing the inactivated virus fluids with an adjuvant. The amount of virus per dose of vaccine is equivalent to from approximately $10^4$ to $10^8$ 50% cell culture infective doses per ml ($CCID_{50}$ml). In addition, other viruses or bacteria may be included such as, but not limited to, canine adenovirus type 2, canine parainfluenze virus, canine parvovirus, *Leptospira canicola* and *Leptospira icterohaemorrhagiae*. The vaccine may be administered subcutaneously or intramuscularly. The vaccine inoculation volume will range from about 0.5 ml to 4 ml. Normally 2 injections are given at from 1 to 3 week intervals.

Preferably the dosage of the inactivated canine distemper virus is from about $10^4$ to about $10^8$ $CCID_{50}$/ml, that is, cell culture infective dose/ml. More preferably, within the range of from about $10^5$ to about $10^7$ $CCID_{50}$/ml and most preferably within the range of about $10^{5.8}$ to about $10^{6.2}$ $CCID_{50}$/ml.

The following examples are offered to further illustrate but not limit both the composition of the invention, the method of preparation of the composition of the invention, and the method of use of the composition of the invention to immunize the mammals against canine distemper virus.

EXAMPLES

EXAMPLE 1

Virus Growth, Assay and Inactivation

This example illustrates how the canine distemper virus was grown, assayed, and inactivated using a furocoumarin inactivation technique.

A. Production of Virus and Tissue Culture

Canine cells (DKF), a dog kidney cell line, or (DK) tertiary dog kidney cells are grown as monolayers in plastic cell culture vessels in Eagle's Minimum Essential Medium with Earle's salts and non-essential amino acids (MEN) supplemented with 5% heat inactivated fetal bovine serum or 5% heat inactivated calf serum. Cell cultures are used to produce live CDV from master seed virus. Cells are grown in culture vessels to 80% to 100% confluency (approximately $2 \times 10^5$ cells per cm$^2$ of growth surface area) using standard mammalin cell culture techniques. Generally, plastic roller bottles (e.g. Corning No. 25140-850) with a growth surface area of 850 cm$^2$ containing 100 ml of MEN supplemented with 5% fetal bovine serum and $1 \times 10^8$ to $2 \times 10^8$ cells/bottle are used of virus production although other permissive cells, other culture vessels, other culture media or other supplements may be used. The cell cultures are initiated by seeding approximately $1 \times 10^7$ to $2 \times 10^7$ cells into 100 mls of growth medium in a roller bottle on a roller bottle rotator at 0.25 to 2 rpm at 35° to 38° C. The cultures are grown to 80% to 100% confluency over a seven to ten day period with a medium change every three to five days.

When the monolayers are 80% to 100% confluent the culture medium is removed. Two hundred mls of MEN supplemented with 0.5lactalbumin hydrolysate (e.g. GIBCO 670-1800) is added per roller bottle. Monolayers are infected with $10^5$ to $10^6$ $CCID_{50}$ of CDV per roller bottle. The multiplicity of infection (MOI) is approximately 0.01. The MOI may range from 0.001 to 0.05. The post-infection incubation is at 35° to 38° C. with rotation. Two to five days post-infection, CDV cytopathic effect (CPE) is evident. Two days post-infection, the CPE is characterized by the appearance of some vacuolated cells and some multi-nucleated giant cells. On day five post-infection, giant cells are more numerous. On day five post-infection, the medium containing virus is harvested from the roller bottle. The roller bottle is fed 200 ml fresh MEN supplemented with 0.5% LAH and incubated at 35° to 38° C. with rotation for an additional three days. During the six to eight day post-infection period, the CPE progresses to the point that many cells are shed into the medium. By day eight post-infection, 50% to 90% CPE is evident. On day eight post-infection, the medium containing virus is harvested.

The virus preparation may be concentrated by ultrafiltration using a Pellicon cassette system (Millipore XX42ASY60) with a cassette having a nominal exclusion of $10^5$ daltons (Millipore PTHK000C5). The Pellicon cassette system is sterilized by filling the assembled unit with 1 N NaOH and incubating the unit 12 to 14 hours at room temperature. The NaOH solution is pumped out of the cassette system and the system is flushed with two or four liters of sterile $H_2O$. The assembly and operation of the Pellicon system are in accordance with the instruction furnished by the manufacturer. All steps in the concentration are preformed aseptically.

B. Virus Assay

Ten-fold serial dilutions of a virus sample are made by adding 0.1 ml of the virus sample to 0.9 ml of MEN supplemented with 5% F$^i$. Eight chamber Lab-Tek slides are seeded with 0.4 ml/chamber of DKF cells at $1.5 \times 10^5$ cells/ml in MEN supplemented with 5% F$^i$ (approximately $6 \times 10^4$ cells/chamber). Immediately following seeding of cells, 0.1 ml aliquots of each serial dilution are added to each of five chambers. The slides are incubated at 35° to 38° C. in 5% $CO_2$ in air for six days. On day six, remove the medium, plastic chamber and gasket from the slide. Rinse slides once in PBS, fix in acetone at $-20°$ C. for 20 minutes and air dry. Anti-CDV FITC conjugate (0.1 ml) is placed on each slide and a coverslip is placed on the monolayer to spread the conjugate over the entire cell sheet. Slides are incubated in a high humidity incubator for 30 minutes at 35° to 37° C. Coverslips are removed in $3 \times 3$ minute rinses in PBS at room temperature. Slides are counter stained for 90 seconds in Evans blue, rinsed twice for 3 minutes in PBS, rinsed in distilled water and placed in a modified X-ray dryer until dry. Coverslips are mounted on slides using mounting fluid (80% gylcerol in PBS, v/v). Cells are examined for flourescence typical of CDV which constitutes a positive response. End point is calculated by the method of Reed and Muench.

C. CDV Inactivation

1. Psoralen Inactivation

One hundred ml of CDV is pipetted into a sterile container. One ml of 8-methoxypsoralen (8-MOP, 10 mg/ml in dimethyl sulfoxide) and one ml of ascorbate stock solution (1M ascorbate in sterile de-ionized $H_2O$ are added to the container. The mixture is incubated 15 minutes in a 37° C. water bath. After incubation the mixture is transferred to another sterile vessel and allowed to equilibrate in an argon atmosphere for 5 minutes. After equilibration the mixture is placed under a long wavelength ultraviolet light source at a temperature of 10° C. for 2 hours. The incident light intensity is approximately 15 $mW/cm^2$.

After the irradiation is completed, the mixture is removed from the light source and an additional 1 ml of 8-MOP stock solution and 1 ml of ascorbate stock solution is added to virus. The mixture is again incubated 15 minutes in 37° C. water bath. After incubation the mixture is transferred to sterile vessel and allowed to equilibrate in an argon atmosphere for 5 minutes and irradiated as described above for an additional 2 hours. This procedure is repeated one more time until three additions (a total of approximately 300 micrograms/ml) of 8-MOP have been performed, and the virus sample has been irradiated for at least six hours.

The inactivated virus is now ready for use in preparation of vaccine. While the inactivation procedure described here is the preferred furocoumarin procedure, specifically using 8-methoxypsoralen, other inactivation procedures as mentioned earlier may be used. Also, as indicated by the examples shown below, there has been successful inactivation with binary ethyleneimine to produce inactivated CDV vaccine. In the binary ethyleneimine inactivation procedure, the following technique is offered as illustrative.

2. BEI Inactivation

A 0.2 molar solution of bromoethylamine hydrobromide (BEA) is prepared by dissolving 3.55 grams in 71 ml distilled water. 56.8 ml of BEA solution is added to 14.2 ml 1.0 normal sodium hydroxide solution. Binary ethyleneimine (BEI) is formed by incubating the above mixture for 1 hour at 36° C. 1343 ml of harvested canine distemper virus fluids are brought to 37° C., to which the BEI solution is added while the suspension is stirred. The inactivation is continued by incubation at 37° C. for 28 hours. The BEI is then neutralized by the addition of 46.2 ml of a 50% solution of sodium thiosulfate.

To confirm complete viral inactivation, whether psoralen or BEI is used, two ml of the inactivated virus fluids are tested for the presence of residual live virus by inoculation onto a 150 $cm^2$ monolayer of dog kidney cells. Inoculated cells are incubated for 7 days, then are subpassaged. If cytopathic effects due to CDV infection are not observed during the first or second in vitro passages, it is concluded virus fluids do not contain residual live CDV.

EXAMPLE 2

Testing of Immunological Response

Binary ethyleneimine inactivated CD virus of the preferred Rockborn strain was used to formulate vaccine with adjuvant B. The binary ethyleneimine inactivation procedure was performed as described in Example I.

Five dogs, (CDV sero-negative) identified as numbers 29, 65, 68, 71 and 72, were vaccinated twice at a 21-day interval with a 1.0 ml dose of BEI-inactivated CDV vaccine containing $10^{5.9}$ $CCID_{50}$ of the Rockborn strain of CDV and 50% Adjuvant B. Serum was collected for serologic evaluation at the time of inoculations and at 14 days following the second vaccination.

In vitro virus neutralization of CDV by sera collected was examined using a 50% plaque reduction test (Table I). Positive and negative control sera behaved as expected.

TABLE I

VIRUS NEUTRALIZATION DATA FROM DOGS VACCINATED WITH BEI-INACTIVATED CDV

| Animal # | Antibody Response Day of Test | | |
|---|---|---|---|
| | 0 | 21 | 35 |
| 29 | <4 | 18 | 162 |
| 65 | <4 | <4 | 54 |
| 68 | <4 | 18 | 54 |
| 71 | <4 | 2 | 54 |
| 72 | <4 | 18 | 54 |

Table I shows anti-canine distemper serum neutralizing antibody as determined by a constant viru/serum dilution in vitro neutralization test. This is a conventional procedure and for details concerning it, see Ross and Friedman's *Manual of Clinical Immunology*, which is incorporated herein by reference. Table I provides the antibody titers from the five vaccinated dogs and demonstrates successful immunization.

EXAMPLE 3

Challenge Test of Vaccinated Dogs

Twenty-two dogs seronegative to CDV were vaccinated intramuscularly (IM) with a psoralen-inactivated CDV vaccine prepared as in Example 1, given in two 1 ml doses, 21 days apart. The vaccine was formulated with 50% Adjuvant B. On experimental day 35, vaccinated and 5 nonvaccinated seronegative dogs were challenged with virulent CDV.

Serum samples for serologic evaluation were collected from vaccinated dogs on days 0, 21 and 35. Geometric mean titers are shown in Table II, demonstrating successful immunization.

Clinical signs were not observed in vaccinated dogs following vaccination. Dogs were challenged by oral nasal installation of $10^6 CCID_{50}$ of virulent canine distemper vaccine. Following challenge, vaccinated and control dogs were observed for 21 days for clinical signs of disease which were assigned points using a clinical reaction index (Table III).

The clinical reaction scores for vaccinated and control group dogs are summarized in Table IV. Four of five control dogs experienced severe illness, including one fatal infection, in contrast to vaccinated dogs in which clinical signs were, at most, mild and transient. This demonstrates the efficacy of the inactivated CDV vaccine.

TABLE II

RECIPROCAL GEOMETRIC MEAN VIRUS NEUTRALIZATION TITERS FROM DOGS VACCINATED WITH A PSORALEN-INACTIVATED CDV VACCINE

| Group | Day of Test | | |
|---|---|---|---|
| | 0 | 21 | 35 |
| I - Vaccinates (n = 22) | <2 | <6 | 139 |
| II - Controls | ND* | $<2^a$ | $<2^b$ |

*ND = Not Done
$a_n = 5$
$b_n = 4$

TABLE III

CANINE DISTEMPER VACCINE - PSORALEN-KILLED VIRUS KEY TO SCORING CLINICAL OBSERVATIONS

| | | |
|---|---|---|
| Anorexia (Q) | 1-2 days = | 1 pt |
| | ≧3 days = | 2 pts |
| Dehydration (DH) | 1-2 days = | 2 pts |
| | ≧3 days | 2 pts |
| Depression (DP) | 1-2 days = | 2 pts |
| | 3-5 days = | 4 pts |
| | ≧6 days = | 6 pts |
| Diarrhea (B) | each day = | 2 pts |
| Bloody Diarrhea (BB) | each day = | 3 pts |
| Eye Discharge-Serous (CS) | 1-3 days = | 1 pt |
| | ≧4 days = | 2 pts |
| Eye Discharge - | 1=2 days = | 2 pts |
| Mucopurulent (CM or CP) | 3-5 days = | 4 pts |
| | 3-5 days = | 4 pts |
| | ≧6 days = | 6 pts |
| Nasal Discharge - Purulent (PP) | 1-2 days = | 2 pts |
| | 3-5 days = | 4 pts |
| | ≧6 days = | 6 pts |
| Weakness | 1-2 days = | 1 pt |
| | ≧3 days = | 2 pts |
| Death due to distemper challenge | | 30 pts |

TABLE IV

SUMMARY OF CUMULATIVE CLINICAL OBSERVATION SCORES POST CHALLENGE

| Group | Mean Clinical Score | Range |
|---|---|---|
| 1 - Vaccinates (n = 22) | 0.95 | 0-5 |
| 2 - Controls (n = 5) | 30.8 | 2-53 |

The above methods for assaying vaccine virus, viral inactivation, and testing of immunological responses and challenge testing demonstrates both preparation and successful use of the canine distemper vaccine of this invention. It also represents the first ever efficacious successful inactivated canine distemper vaccine. It therefore can be seen that the invention accomplishes at least all of its stated objectives.

It should, however, be mentioned that there may be some modifications of both the inactivation procedure, the dose procedure, and of the other techniques illustrated in this invention, which are intended to come within the spirit and scope of this invention. Thus, the examples are offered as illustrative and not necessarily invention limiting.

What is claimed is:

1. A process of inactivating canine distemper virus which allows said virus to test negatively for residual live canine distemper virus and to substantially retain its immunogenicity, said process comprising:
exposing said virus to a small but inactivating effective amount of binary ethyleneimine at a temperature ranging from about −10° C. to about 40° C. for a time sufficient to render said virus non-infectious.

2. The process of claim 1 wherein the dose amount of said inactivated canine distemper virus is from about $10^4$ to about $10^8$ $CCID_{50}$/ml.

3. The process of claim 1 wherein the dose amount of said virus is from about $10^5$ to about $10^7$ $CCID_{50}$/ml.

4. The process of claim 1 wherein the dose amount of said virus is from about $10^{5.8}$ to about $10^{6.2}$ $CCID_{50}$/ml.

5. The process of claim 1 wherein said virus includes oil emulsion adjuvant.

6. The process of claim 1 wherein said canine distemper virus is the Rockborn strain.

7. A process of claim 1 wherein said canine distemper virus is grown in cultured mammalian host cells prior to inactivation.

8. A process of inactivating canine distemper virus of the Rockborn strain, which allows said virus to test negatively for residual live canine distemper virus and to substantially retain its immunogenicity, said process comprising: exposing canine distemper virus of the Rockborn strain to a small but inactivating effective amount of binary ethyleneimine at a temperature ranging from −10° C. to about 40° C. for a time sufficient to render said virus noninfectious, but still immune response effective.

* * * * *